United States Patent [19]

Inamoto et al.

[11] 4,087,467
[45] May 2, 1978

[54] 8-EXO-HYDROXYMETHYL-ENDO-TRICYCLO [5.2.1.0²,⁶]DECANE

[75] Inventors: Yoshiaki Inamoto; Yoshiaki Fujikura; Hiroshi Ikeda, all of Wakayama, Japan

[73] Assignee: Kao Soap Co., Ltd., Tokyo, Japan

[21] Appl. No.: 744,956

[22] Filed: Nov. 26, 1976

[30] Foreign Application Priority Data

Dec. 4, 1975 Japan ................ 50-144674

[51] Int. Cl.² .................. C07C 35/22; C07C 29/14
[52] U.S. Cl. ................................................ 568/817
[58] Field of Search ................ 260/617 F, 617 C

[56] References Cited

U.S. PATENT DOCUMENTS

| | | | |
|---|---|---|---|
| 2,394,583 | 2/1946 | Bruson | 260/617 F |
| 2,404,787 | 7/1946 | Bruson | 260/617 F |
| 2,841,614 | 7/1958 | Buchner et al. | 260/617 F |
| 2,875,244 | 2/1959 | Bartlett et al. | 260/617 F |
| 3,345,416 | 10/1967 | Tinsley et al. | 260/617 F |
| 3,776,940 | 12/1973 | Just et al. | 260/617 F |
| 4,002,691 | 1/1977 | Shepherd, Jr. | 260/617 F |

OTHER PUBLICATIONS

Weygand, "Prep. Org. Chem.", pp. 45-46 (1972) John Weley & Sons.
Patar, "Chem. of the Carbonyl Group", pp. 510-514 (1966) Interscience.

*Primary Examiner*—Norman Morgenstern
*Attorney, Agent, or Firm*—Blanchard, Flynn, Thiel, Boutell & Tanis

[57] ABSTRACT

8-exo-hydroxymethyl-endo-tricyclo [5.2.1.0²,⁶] decane is prepared by hydrogenating 8- and 9-exo-formyl-endo-tricyclo [5.2.1.0²,⁶] deca-3-enes.

1 Claim, No Drawings

8-EXO-HYDROXYMETHYL-ENDO-TRICYCLO [5.2.1.0$^{2,6}$]DECANE

FIELD OF THE INVENTION

The present invention relates to 8-exo-hydroxymethyl-endo-tricyclo [5.2.1.0$^{2,6}$] decane.

Further, the present invention relates to a process for preparing 8-exo-hydroxymethyl-endo-tricyclo [5.2.1.0$^{2,6}$] decane of formula (I):

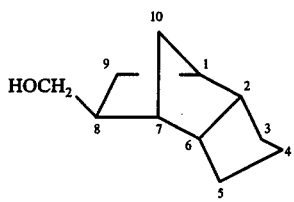

characterized by hydrogenating 8- and 9-exo-formyl-endo-tricyclo [5.2.1.0$^{2,6}$] deca-3-enes of formula (II):

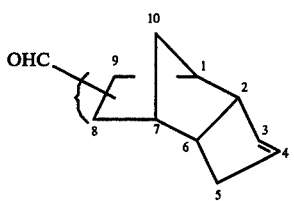

in the presence of platinum oxide, Raney nickel or the like as catalyst under elevated hydrogen pressure.

SUMMARY OF THE INVENTION

From 8-exo-hydroxymethyl-endo-tricyclo [5.2.1.0$^{2,6}$]-decane of formula (I), 4-homoisotwistane (tricyclo [5.3.1.0$^{3,8}$]-undecane (III)) can be derived at a high selectivity by hydride transfer reduction rearrangement:

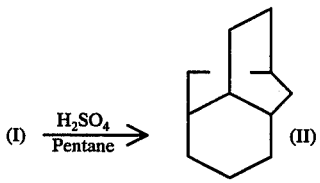

It has been revealed already by the inventors that various derivatives derived from the compound of formula (III) exhibit various physiological effects such as typical antiviral effects and they can be used for many useful purposes, for example, in Japanese Patent Application No. 93968/1975. The compound of formula (I) obtained by the invention is very important starting material for the synthesis of those useful compounds.

The catalyst of the present invention is one of those used for hydrogenation of olefins and aldehydes, such as compounds of platinum, palladium, nickel, cobalt, iron, copper, for example, platinum oxide, Raney nickel or the like.

In carrying out the process of the present invention, the catalyst is used in a weight ratio of the catalyst to starting material (II) of higher than 1/100,000 to 1/1; weight ratio of from 1/1,000 to 1/10 is preferred for attaining a suitable reaction velocity.

A solvent is not necessarily used, but a lower alcohol of $C_1$ to $C_4$ such as methanol, ethanol, n-propanol or i-propanol or an ether solvent such as diethyl ether or tetrahydrofuran may be used.

The reaction temperature ranges from room temperature to +200° C, preferably 30°–150° C. The first step of the reaction can be carried out at room temperature without necessitating any special heating, since it is hydrogenation in the 3(4) position of the olefinic starting material of formula (II). Then, hydrogenation reaction of the aldehyde is carried out under heating at a temperature preferably in the range of from +30° C to +200° C, more preferably 50°–150° C. The hydrogen pressure is in the range of 10–200 atms., preferably 50–100 atms.

The starting material of formula (II) of the present invention can be synthesized, for example, by oxo reaction of endo-tricyclo [5.2.1.0$^{2,6}$] deca-3,8-diene in the presence of a rhodium triaryl phosphine catalyst. The structure thereof has been proved by the inventors.

EXAMPLE 149.6 Grams (0.9 mole) of 8- and 9-exo-formyl-endo-tricyclo [5.2.1.0$^{2,6}$] deca-3-ene, 100 ml. of methanol and 200 mg of platinum oxide are charged in a pressure vessel. Air in the vessel is replaced with hydrogen. The mixture is stirred at room temperature under a hydrogen pressure of 90 atms. After hydrogen absorption ceases, the reaction temperature is raised to 120° C and hydrogenation is continued further until hydrogen absorption ceases again. After completion of the reaction, the catalyst is filtered out and the filtrate is distilled out under reduced pressure to obtain a colorless, viscous oily product.

Boiling point: 95°–96° C/0.3 mmHg, $D^{28}=1.5129$

Elementary analysis: Found: C 79.2; H 10.5%. Theoretical (as $C_{11}H_{18}O$): C 79.5; H 10.9%.

IR (liquid film, cm$^{-1}$) 3600–3100(O-H), 1470, 1450, 1020(C-O).

NMR (CCl$_4$ solvent, TMS internal standard, δ). 4.3(OH), 3.3(CH$_2$O, d, J=7Hz), 2.5–0.9(15H, complex multiplet).

MS 166(1.9 M+), 148(13), 135(100), 107(13), 93(16), 91(13), 81(19), 80(22), 79(28), 67(47), 41(12).

REFERENTIAL EXAMPLE

66 Grams (0.5 mole) of endo-tricyclo [5.2.1.0$^{2,6}$]3,8-diene, 100 ml. of benzene, 345 mg (0.0005 mole) of [RhCl(CO) (PPh$_3$)$_2$] and 0.25 ml. of triethylamine are charged in an autoclave. Air in the autoclave is replaced with carbon monoxide gas and 100 atms. of a mixture of carbon monoxide and hydrogen (1:1 molar ratio) are added thereto. Reaction temperature is kept at 70° C under stirring and reaction is effected till 1.2 equivalents of the gas are absorbed. After completion of the reaction, the vessel is cooled and the reaction mixture is taken out. After removing the solvent, the product is subjected to distillation to obtain 8- and 9-exo-formyl-endo-tricyclo [5.2.1.0$^{2,6}$] undeca-3-ene (66.4 g; yield 82%) as colorless oily product.

Boiling point: 77° C/0.6 mmHg

Elementary analysis: Found: C 81.5; H 8.8%. Theoretical (as $C_{11}H_{14}O$): C 81.4; H 8.7%.

IR (liquid film cm$^{-1}$) 3140(=C—H), 2800, 2700(CHO), 1720(C=O), 1610(C=C), 800, 740.

PMR (CCl$_4$ solvent, TMS internal standard, δ) 9.52(CHO, 1H), 5.5(—CH=CH—, 2H, complex multiplet) 3.40–0.95(11H, complex multiplet)

$^{13}$CNMR (CDCl$_3$ solvent, TMS internal standard) 22.2, 25.9, 32.2, 32.4, 38.6, 38.9, 39.4, 40.5, 41.3, 42.2, 42.5, 47.5, 50.5, 52.6, 53.0, 130.4 131.8, 132.2, 132.5, 203.2, 203.8.

MS, M/E (relative intensity) 162(21), 96(21), 95(31), 91(31), 79(25), 77(24), 67(93), 66(100), 41(27), 39(36).

The starting mixture of 8- and 9-formyl-endo-tricyclo [5.2.1.0$^{2,6}$] deca-3-enes (Formula II) can be prepared as described in the application of Yoshiaki Inamoto, Yoshiaki Fujikura and Hiroshi Ikeda entitled "8- and 9-Exo-Formyl-Endo-Tricyclo [5.2.1.0$^{2,6}$] Deca-3-Enes," Ser. No. 744,955, filed Nov. 26, 1976, now abandoned corresponding to Japanese Ser. No. 144675, filed Dec. 4, 1975). The formula I compound can be transformed to the formula II compound tricyclo [5.3.1.0$^{3,8}$] undecane, a known useful compound, as described in an application of Yoshiaki Inamoto, Yoshiaki Fujikura, Kiyoshi Tsuchihashi and Eiji Kashihara entitled "Process for Hydride Transfer Reduction Rearrangement of 8-Exo-Hydroxymethyl-Endo-Tricyclo [5.2.1.0$^{2,6}$] Decane" Ser. No. 744,957, filed Nov. 26, 1976, now U.S. Pat. No. 4,059,643, corresponding to Japanese Ser. No. 144673/75, filed Dec. 4, 1975). The entire contents of these two applications are incorporated herein by reference.

The embodiments of the invention in which an exclusive property or privilege is claimed are defined as follows:

1. 8-exo-hydroxymethyl-endo-tricyclo [5.2.1.0$^{2,6}$] decane.

* * * * *